United States Patent [19]

Gorman et al.

[11] 4,293,706

[45] Oct. 6, 1981

[54] PREPARATION OF N-BENZYLOXYCARBONYL ASPARTIC ACID

[75] Inventors: Susan B. Gorman, Barrington; Ralph B. Thompson, Oakbrook; Edward E. Yonan, Carol Stream, all of Ill.

[73] Assignee: PPG Industries, Inc., Pittsburgh, Pa.

[21] Appl. No.: 161,175

[22] Filed: Jun. 19, 1980

[51] Int. Cl.$^3$ .......................................... C07C 125/06
[52] U.S. Cl. ..................................................... 560/163
[58] Field of Search .......................................... 560/163

[56] References Cited

U.S. PATENT DOCUMENTS

| | | | |
|---|---|---|---|
| 3,259,617 | 7/1966 | Sheehan | 260/112.5 |
| 3,492,131 | 1/1970 | Schlatter | 99/141 |
| 3,592,836 | 7/1971 | Ugi | 260/463 |
| 3,642,491 | 2/1972 | Schlatter | 99/28 |
| 3,714,139 | 1/1973 | Schlatter | 260/112.5 |
| 3,800,046 | 3/1974 | Schlatter | 426/168 |
| 3,808,190 | 4/1974 | Dahlmans | 260/112.5 |
| 3,887,538 | 6/1975 | Shields | 260/112.5 |
| 4,165,311 | 8/1979 | Isowa | 260/112.5 R |
| 4,181,649 | 1/1980 | Matsushita | 260/112.5 R |

OTHER PUBLICATIONS

Howbon-Weyl, vol. XV/1, p. 321 (1974).
Beryann, Berichte, 65, p. 1192-1201 (1932).

*Primary Examiner*—Natalie Trousof
*Assistant Examiner*—Michael Shippen
*Attorney, Agent, or Firm*—Irwin M. Stein

[57] ABSTRACT

N-Benzyloxycarbonyl aspartic acid substantially free of N-benzyloxycarbonyl aspartyl aspartic acid is prepared by introducing benzyl chloroformate gradually into an aqueous solution of the disodium salt of aspartic acid at temperatures of between 10° C. and about 45° C. while maintaining the pH of the aqueous solution at between 10.75 and 11.75. In a further embodiment, the mole ratio of unreacted benzyl chloroformate to the aspartic acid salt in the reaction medium is maintained preferably at no greater than 0.2. The resulting reaction mixture is acidified, e.g, with hydrochloric acid, to convert the reaction product to the free acid, which is separated from the reaction mixture, washed with water and dried to yield an essentially pure white granular product.

15 Claims, No Drawings

PREPARATION OF N-BENZYLOXYCARBONYL ASPARTIC ACID

DESCRIPTION OF THE INVENTION

The lower alkyl esters of α-L-aspartyl-L-phenylalanine that have 1 to 4 carbon atoms in the alkyl group have a taste closely resembling that of sugar and are, therefore, valuable sugar substitutes. See, for example, U.S. Pat. No. 3,492,131. One such dipeptide, i.e., L-aspartyl-L-phenylalanine methyl ester (aspartame), is described as 100 to 200 times as sweet as sucrose. The aforementioned dipeptide esters are conveniently manufactured from the aspartic acid derivative wherein the amino function is protected by a benzyloxycarbonyl group, the β-carboxy function is protected by a benzyl ester group, and the α-carboxy group is protected by a p-nitrophenyl ester group. The preparation of that aspartic acid derivative is described by S-Guttmann in Helv. Chim. Acta, 44, 721 (1961). Further reaction of that derivative with a phenylalanine ester, e.g., L-phenylalanine methyl ester, produces a protected dipeptide which when subjected to hydrogenolysis produces the lower alkyl ester, e.g., the methyl ester of L-aspartyl-L-phenylalanine. The aforesaid aspartic acid derivative can be prepared from N-benzyloxycarbonyl-L-aspartic acid.

The ultimate use of the aforementioned dipeptide sweetening agents in edible materials requires that aspartic acid derivatives utilized as precursers in the synthesis of the dipeptide sweetening agent be as pure as possible. Thus, it is most desirable that such precursers be substantially free of by-products formed during their chemical synthesis.

It has now been discovered that the aspartic acid derivative, N-benzyloxycarbonyl aspartic acid, can be prepared substantially free of N-benzyloxycarbonyl aspartyl aspartic acid (a by-product) and at least 97 percent pure by reaction of the alkali metal salt of aspartic acid with benzyl chloroformate under carefully controlled reaction conditions of temperature and pH. In particular, it has been discovered that N-benzyloxycarbonyl aspartic acid containing less than 0.2 weight percent N-benzyloxycarbonyl aspartyl aspartic acid can be prepared by adding gradually a substantially stoichiometric amount of benzyl chloroformate to an aqueous solution of alkali metal salt of aspartic acid while maintaining the temperature of the aqueous solution at between 10° C. and 45° C. and the pH of the aqueous solution at between 10.75 and 11.75. Departure from the aforesaid conditions provides an environment in which side reactions have a greater opportunity to occur. In a preferred embodiment, the benzyl chloroformate rate of addition is such that the mole ratio of unreacted benzyl chloroformate to the aspartic acid salt in the reaction mixture is not greater than 0.2. The resulting reaction mixture is acidified with, for example, hydrochloric acid to convert the alkali metal salt of N-benzyloxycarbonyl aspartic acid to the free acid, which is recovered, washed and dried.

DETAILED DESCRIPTION

The reaction of aspartic acid with benzyl chloroformate has been described in the literature. See, for example, the article, "Concerning a Universal Process for the Synthesis of Peptides" by Max Bergmann et al, Berichte d.D. Chem. Gesellschaft, Volume 65, pages 1192–1201, 1197 (1932) and Houben-Weyl, Volume XV/1, page 321 (1974). The reaction is also described in Example 1 of U.S. Pat. No. b 3,808,190. However, the processes described in the aforementioned literature do not describe the reaction conditions that have been found necessary for the preparation of N-benzyloxycarbonyl aspartic acid (hereinafter Z-Asp) substantially free of N-benzyloxycarbonyl aspartyl aspartic acid (hereinafter Z-Asp Asp).

In the herein described process for the preparation of Z-Asp, benzyl chloroformate is charged gradually to a reaction vessel containing an aqueous solution of a dialkali metal salt of aspartic acid under carefully controlled conditions of pH and temperature. The pH of the aqueous solution is maintained at between about 10.75 and 11.75 during addition of the benzylchloroformate. Preferably, the pH is maintained at between about 11.5 and 11.75. At a pH significantly greater than 11.75, e.g., between 12 and 13.5, significant hydrolysis of the benzyl chloroformate reactant to benzyl alcohol occurs and the Z-Asp product is found to contain more than trace amounts of impurities that are less polar than Z-Asp, as determined by thin layer chromatography (TLC). The yield of Z-Asp is also reduced when the reaction is conducted at a high pH, i.e., a pH of 12 to 13.5. When the pH of the aqueous solution is significantly less than 10.75, e.g., between about 7 and 9, significant quantities, e.g., from about 5 to about 16 weight percent (basis Z-Asp) of Z-Asp Asp as well as impurities less polar and more polar than Z-Asp, as determined by TLC, are found in the Z-Asp product.

As described hereinabove, the pH of the aqueous solution in which the reaction is conducted is maintained at between about 10.75 and 11.75 during addition of the benzyl chloroformate reactant, i.e., during the reaction. It should be recognized, however, that the reaction mixture is a heterogeneous system, and, as with any dynamic system, i.e., a system in a state of constant change, excursions of short duration beyond the desired pH range can occur and are contemplated. Such excursions of pH are not considered detrimental to the described invention provided that they are of relatively short duration. Use of the term "maintained" or terms of similar import in the specification and claims are intended to mean and include such pH excursions.

The pH of the aqueous solution within the reactor is maintained within the range of 10.75 and 11.75 by the addition of a water soluble, inorganic alkaline reagent simultaneously with the addition of the benzyl chloroformate reactant. The alkaline reagent must be capable of neutralizing the hydrogen chloride liberated during the reaction and maintaining the reaction mixture at the desired pH. It is preferred that the alkaline reagent be identical to that used to form the alkali metal aspartic acid salt reactant. The use of magnesium and calcium oxide as the alkaline reagent result respectively in a Z-Asp product of lower purity than desired and a flocculant precipitate, which causes an incomplete reaction. The use of a sodium carbonate solution as the alkaline reagent results in foaming of the reaction mixture and a more difficult work-up of the product. Thus, it is preferred that the alkaline reagent used be the alkali metal hydroxides, i.e., sodium hydroxide or potassium hydroxide.

The amount of alkaline reagent added to the reaction mixture to maintain the desired pH preferably will be stoichiometrically equivalent to the amount of hydrogen chloride by-product formed during the reaction.

However, a slight stoichiometric excess can be used provided that the pH of the reaction mixture does not exceed and remain above 11.75. Thus, in the case of sodium hydroxide, at least one mole of sodium hydroxide will be added for each mole of hydrogen chloride formed during the reaction. The rate at which the alkaline reagent is added to the reaction mixture will be the rate required to maintain the aqueous solution in the reactor within the desired pH range. The concentration of the alkaline reagent used is not critical. In the case of sodium or potassium hydroxide, it is common to utilize between a 20 and 50 weight percent solution thereof.

The above-described reaction can be conducted at temperatures between about 10° C. and about 45° C. Preferably, the temperature of the reaction is conducted at between 20° C. and 30° or 40° C., more preferably, between 20° C. and 25° C., i.e., at about room temperature. The rate at which the reaction proceeds is a direct function of the temperature used. However, as the temperature increases within the aforesaid range, the amount of impurities, e.g., less polar to non-polar impurities, found in the Z-Asp product tends to increase. Significant levels of impurities do not appear in the product, as measured by TLC, until temperatures of at least about 45° C. are reached. At temperatures of less than about 10° C., the reaction proceeds at commercially impractical rates.

The benzyl chloroformate reactant used in the present process is available commercially. It is added slowly and with appropriate agitation to the reaction mixture in order to avoid the presence of excessive or localized quantities of unreacted benzyl chloroformate within the reaction mixture. Sufficient agitation to promote intimate contact between the reactants should be used. In a preferred embodiment, the rate at which benzyl chloroformate is introduced into the reaction mixture is controlled so that the mole ratio of unreacted benzyl chloroformate to the aspartic acid salt therein is not greater than 0.2, preferably not greater than 0.15 and most preferably not greater than 0.1. It is contemplated also that lower alkyl, i.e., $C_1$-$C_4$, nuclear substituted benzyl chloroformates can be used as the benzyl chloroformate reactant. Examples of such substituents include meta- or para- substituted methyl or ethyl substituted benzyl chloroformate. Results similar to those obtained with benzyl chloroformate are expected for the reason that the alkyl substituents are not expected to alter the chemical reactions described.

The addition of benzyl chloroformate to the reaction mixture at a rate which results in significant quantities of unreacted benzyl chloroformate in the reaction mixture, e.g., by adding the benzyl chloroformate all at once, results in hydrolysis of more than a minor portion of the benzyl chloroformate. The resulting benzyl alcohol forms esters with acidic materials, i.e., carboxylic acid containing materials, that may be present within the reaction mixture. These esters are believed to be the less polar impurities found by TLC in the Z-Asp product. It has been found that the addition gradually and uniformly of benzyl chloroformate to the reactor over a period of at least about 2 hours, e.g., 2 to 3 hours, is sufficient to maintain the mole ratio of unreacted benzyl chloroformate to aspartic acid salt in the reaction mixture at less than the above described level of 0.2 and to control the rate at which heat is generated by the reaction.

The aspartic acid used in the present process is available commercially as the D(−), L(+) or DL isomers. Any of the aforementioned isomers can be used in the present process. For use in preparing sweetening agents, the L(+) stereoisomer is preferred (the DL isomer mixture being less preferred) for the reason that the L-stereoisomer appears to provide the sweetening properties desired.

In accordance with the present process, benzyl chloroformate is added to an aqueous solution of an alkali metal salt of aspartic acid. The aforementioned aqueous solution can be prepared by adding alkali metal hydroxide to an aqueous slurry of the acid. As used in the present specification and claims, the term "alkali metal" is intended to mean and include sodium and potassium. In order to obtain an aqueous aspartic acid alkali metal salt solution having the desired pH of from about 10.75 to 11.75, it is necessary to utilize an alkaline reagent of sodium or potassium that will provide an aqueous solution within the aforesaid range. Sodium hydroxide and potassium hydroxide are examples of such reagents. The carbonate and bicarbonate salts of sodium and potassium are not usually useful for providing the desired salt solutions for the reason that they typically produce a solution with too low of a pH.

In preparing the aspartic acid salt solution, it is convenient to slurry the aspartic acid in water and subsequently add, e.g., by titration, the alkali metal to the slurry hydroxide until the desired pH is reached. However, it is possible to add the aspartic acid to an aqueous solution of alkali metal hydroxide. The aspartic acid is thereby neutralized to form its alkali metal salt, which is water soluble. Slightly more than a stoichiometric amount of alkali metal hydroxide, i.e., sodium or potassium hydroxide, (2 moles of hydroxide per mole of aspartic acid) are required to prepare the aforesaid solution with a pH within the desired range.

The amount of water used to prepare the aspartic acid solution is not critical; however, excessive amounts of water are economically disadvantageous. Therefore, only that amount of water which provides a reaction mixture than can be easily handled should be used. For example, a ratio of 0.55 liters of water per mole of aspartic acid has been found to be suitable. The Z-Asp product is soluble to a degree in water, the degree of solubility being a direct function of the temperature of the solution. Thus, the more water used to prepare the aspartic acid solution, the more product lost when the aqueous phase of the reaction mixture is separated from the product.

In accordance with the present process, the disodium salt of N-benzyloxycarbonyl aspartic acid is prepared according to the following balanced equation:

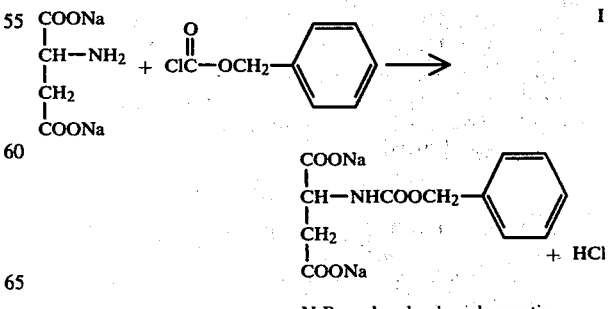

N-Benzyloxylcarbonyl aspartic acid, disodium salt.

Reaction of the sodium salt of N-benzyloxycarbonyl aspartic acid with a further mole of the aspartic acid sodium salt yields following acidification the undesired impurity, N-benzyloxycarbonyl aspartyl aspartic acid (Z-Asp Asp),

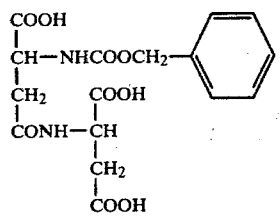

N-Benzyloxycarbonyl aspartyl aspartic acid

Although the aforesaid formula for Z-Asp Asp has been shown as the β-amide it is believed that any Z-Asp Asp impurity formed is likely to be present as both the α- and β-amides.

In accordance with the present process, N-benzyloxycarbonyl aspartic acid (Z-Asp) is prepared substantially free, i.e., less than about 0.2 weight percent, of N-benzyloxycarbonyl aspartyl aspartic acid (Z-Asp Asp). In addition, the desired product is prepared with only minor amounts, i.e., less than an estimated 0.5, usually less than 0.2, weight percent, of other organic impurities, i.e., substances that are less polar and more polar than Z-Asp, as determined by thin layer chromatography (TLC). Use of the more preferred reaction conditions, as described herein, results in the preparation of Z-Asp containing less than about 0.1 weight percent of Z-Asp Asp.

The Z-Asp product produced in accordance with the present process is substantially pure, i.e., it is at least 97 percent (on a weight basis) Z-Asp. Often the product is better than 98 or 99 percent pure. In addition to Z-Asp Asp and the other described organic impurities, the Z-Asp product can contain small amounts (not more than about one percent) of alkali metal salt, e.g., sodium or potassium chloride, and water. The amount of alkali metal salt remaining in the Z-Asp product is controlled, in part, by the thoroughness with which the product is washed, e.g., with water, following its recovery.

After completing the addition of benzyl chloroformate to the reaction mixture, agitation and addition of alkali metal hydroxide are continued until complete reaction of the benzyl chloroformate occurs. About 0.5 to 1 hour (depending on the rate of benzyl chloroformate addition) is required for the reaction to reach completion, which is indicated by stabilization of the pH of the reaction mixture. Stabilization of pH is indicated when no additional alkali metal hydroxide is required to be added to the reaction mixture to maintain the pH thereof within the desired range. Thereafter, the reaction mixture is acidified with cooling to a pH of between about 1.5 and about 2.5 to convert the Z-Asp alkali metal salt product to the free acid. Examples of acids that can be used include hydrochloric acid and sulfuric acid. Preferably, hydrochloric acid is used as the acid so as not to introduce a further anionic species into the reaction medium. Sufficient cooling is provided to compensate for the heat of neutralization.

The Z-Asp product (free acid) in the acidified reaction mixture crystallizes from the reaction mixture and is separated from its mother liquor by conventional separating means, e.g., by means of a filter or centrifuge. The recovered white granular Z-Asp product is washed with water to remove alkali metal salt and dried at temperatures less than its decomposition temperature. Washing of the recovered wet Z-Asp product with an equal weight of water (a larger quantity of water can be used if desired) and drying in vacuum or in a circulating air oven at 40° C. have been found to be satisfactory to obtain an essentially pure product.

The present process is more particularly described in the following examples which are intended as illustrative only since numerous modifications and variations therein will be apparent to those skilled in the art.

EXAMPLE I

To a multi-necked round bottom flask fitted with a thermometer, mechanical stirrer, addition funnels, condenser and pH probe were added 550 milliliters water and 133 grams of L-aspartic acid. The resulting slurry was titrated with 50% aqueous sodium hydroxide using the pH probe and a Beckman model 3500 digital pH meter to a pH of 10.78. While maintaining the resulting solution at 20° C., 175.3 grams of benzyl chloroformate (97%) was slowly added to the flask over two (2) hours. The pH of the solution was maintained within the range of 11.5–11.75 during addition of substantially all the benzyl chloroformate by the simultaneous addition of 50% aqueous sodium hydroxide. During a seven (7) minute period near midway through the addition of the benzyl chloroformate, the pH of the solution exceeded 11.75 and reaches a maximum of 12.38; but, the pH was then brought back into the desired range.

Following addition of the benzyl chloroformate, the reaction mixture was stirred until the pH thereof stabilized (about 5 minutes). While maintaining the reaction mixture at 5°–10° C., concentrated hydrochloric acid was added to the reaction mixture until a pH of 1.7 was attained. The resulting crystalline product was recovered by filtration and the filter cake washed once with an equal weight of water. A portion of the washed filter cake was dried in a circulating air oven at 40° C. overnight. Analysis of this dried product by liquid chromatography indicated the following:

| Z-Asp | 100.7 weight percent |
|---|---|
| Z-Asp Asp | 0.17 weight percent |
| Benzyl alcohol | 0.03 weight percent |

The dried product was also determined to contain about 0.15 weight percent sodium chloride, 0.05 weight percent water, and be about 98.3% Z-Asp. Only trace amounts (no more than an estimated 0.5 weight percent) of less to non-polar and more polar impurities were found by TLC. The total yield of washed and dried product was 249.3 grams, which represented a 93.6% yield.

EXAMPLE II

The procedure of Example I was followed except that the pH of the reaction mixture was maintained in the range of 12–13.5, the temperature was maintained at 25° C., the amounts of the reactants used were: L-aspartic acid—33.25 grams, benzyl chloroformate—43.4 grams, and water—155 milliliters, and the benzyl chloroformate was added to the reaction flask over a period of 1.5–2 hours. Analysis of the dried Z-Asp product indicated that it was 83.5 weight percent Z-Asp, contained less than 0.02 weight percent Z-Asp Asp, about 6 weight percent benzyl alcohol. A greater quantity of less polar to non-polar impurities compared to Example I was found in the product by TLC. The yield of product was about 68%.

EXAMPLE III

The procedure of Example II was followed except that the pH of the reaction mixture was maintained in the range of 7–9. The acidified reaction mixture was oily and product did not readily crystallize out of solution. This reaction mixture was left overnight and a gummy material recovered. The yield of dried product was low and was found to contain 51.8 weight percent Z-Asp, 9.08 weight percent Z-Asp Asp and 3.05 weight percent benzyl alcohol. TLC revealed the presence of many extraneous spots, which indicated the presence of significant quantities of more polar as well as less polar to nonpolar impurities in the product (as compared to the product of Example I).

EXAMPLE IV

The procedure of Example II was followed except that the pH was maintained in the range of 11.0–11.75 and the benzyl chloroformate was added all at once. Analysis of the dried product indicated 87 weight percent Z-Asp, 0.24 weight percent Z-Asp Asp, and 0.82 percent benzyl alcohol. A greater quantity (compared to the product of Example I) of less polar to non-polar impurities was found in the product by TLC.

EXAMPLE V

The procedure of Example I was followed except that the pH was maintained in the range of about 10–10.2 and the amounts of reactants used were: L-aspartic acid—66.5 grams, benzyl chloroformate—87.8 grams and water-310 milliliters. Dried product recovered from this experiment analyzed as follows: Z-Asp—97.6 weight percent, and Z-Asp Asp—0.37 weight percent. Analysis of the product by TLC indicated about the same amount of less polar to non-polar impurities as found in the product of Example I.

The data of Examples I–V show that substantially pure N-benzyloxycarbonyl aspartic acid substantially free of N-benzyloxycarbonyl aspartyl aspartic acid can be prepared when the pH of the reaction mixture is maintained at between 10.75 and 11.75.

Although the present process has been described with reference to specific details of certain embodiments thereof, it is not intended that such details should be regarded as limitations upon the scope of the invention except as and to the extent that they are included in the accompanying claims.

We claim:

1. A method for preparing N-benzyloxycarbonyl aspartic acid substantially free of N-benzyloxycarbonyl aspartyl aspartic acid, which comprises:
   (a) introducing a stoichiometric amount of benzyl chloroformate gradually into an aqueous solution of alkali metal salt of aspartic acid at temperatures of between about 10° C. and about 45° C. while maintaining the pH of the aqueous solution at between 10.75 and 11.75, and
   (b) acidifying the resulting reaction mixture, thereby to produce N-benzyloxycarbonyl aspartic acid substantially free of N-benzyloxycarbonyl aspartyl aspartic acid.

2. The method of claim 1 wherein the aspartic acid is L-aspartic acid.

3. The method of claims 1 or 2 wherein the temperature is between about 20° C. and about 25° C.

4. The method of claims 1 or 2 wherein the pH of the aqueous solution is between about 11.5 and 11.75.

5. The method of claims 1 or 2 wherein the benzyl chloroformate is introduced into the aqueous solution at a rate such that the mole ratio of unreacted benzyl chloroformate to aspartic acid salt in the aqueous solution is not greater than 0.2.

6. The method of claim 5 wherein the mole ratio of unreacted benzyl chloroformate to aspartic acid in the reaction mixture is not greater than 0.1.

7. The method of claim 5 wherein the pH of the aqueous solution is between about 11.5 and 11.75 and the temperature is between 20° C. and 25° C.

8. The method of claims 1 or 2 wherein the aspartic acid product is at least 98% N-benzyloxycarbonyl aspartic acid.

9. The method of claim 7 wherein the aspartic acid product is at least 98% N-benzyloxycarbonyl aspartic acid.

10. The method of claim 7 wherein the N-benzyloxycarbonyl aspartic acid product contains less than 0.1 weight percent N-benzyloxycarbonyl aspartyl aspartic acid.

11. The method of claim 8 wherein the N-benzyloxycarbonyl aspartic acid is separated from the reaction mixture and washed with at least an equal weight of water.

12. The method of claims 1 or 2 wherein the acid used to acidify the reaction mixture is hydrochloric acid or sulfuric acid.

13. A method for preparing the dialkali metal salt of N-benzyloxycarbonyl aspartic acid substantially free of the dialkali metal salt of N-benzyloxycarbonyl aspartyl aspartic acid, which comprises introducing gradually a stoichiometric amount of benzyl chloroformate into an aqueous solution of alkali metal salt of aspartic acid at temperatures of between 10° C. and about 45° C. while maintaining the pH of the aqueous solution at between 10.75 and 11.75.

14. The method of claim 13 wherein the benzyl chloroformate is introduced into the aqueous solution at a rate such that the mole ratio of unreacted benzyl chloroformate to aspartic acid salt in the aqueous solution is not greater than 0.2.

15. A method for preparing N-($C_1$-$C_4$ alkyl) benzyloxycarbonyl aspartic acid substantially free of N-($C_1$-$C_4$ alkyl) benzyloxycarbonyl aspartyl aspartic acid, which comprises:
   (a) introducing a stoichiometric amount of $C_1$-$C_4$ alkyl nuclear substituted benzyl chloroformate gradually into an aqueous solution of alkali metal salt of aspartic acid at temperatures of between about 10° C. and about 45° C. while maintaining the pH of the aqueous solution at between 10.75 and 11.75, and
   (b) acidifying the resulting reaction mixture, thereby to produce N-($C_1$-$C_4$ alkyl) benzyloxycarbonyl aspartic acid substantially free of N-($C_1$-$C_4$ alkyl) benzyloxycarbonyl aspartyl aspartic acid.

* * * * *